United States Patent [19]

Krapcho et al.

[11] 4,085,280

[45] Apr. 18, 1978

[54] 7-AMINOALKYL-3,7-DIARYL-3,3,a,4,5,6,7-HEXAHYDRO-2H-INDAZOLES

[75] Inventors: John Krapcho, Somerset; Chester F. Turk, Kendall Park, both of N.J.

[73] Assignee: E. R. Squibb & Sons, Inc., Princeton, N.J.

[21] Appl. No.: 785,396

[22] Filed: Apr. 7, 1977

[51] Int. Cl.² .................. C07D 231/56; C07D 401/06; C07D 413/06
[52] U.S. Cl. .................... 544/140; 548/369; 260/293.6; 260/268 BC; 260/570.5 CH; 424/248.56; 424/250; 424/267; 424/273 P; 542/429
[58] Field of Search ........................ 544/140; 548/369; 260/293.6, 268 H, 268 BC

[56] References Cited

U.S. PATENT DOCUMENTS 3,926,988  12/1975  Krapcho et al. ...................... 548/369

FOREIGN PATENT DOCUMENTS 2,521,299  11/1975  Germany.

OTHER PUBLICATIONS

Chem. Absts., 84:30958v, (1976).

Primary Examiner—Natalie Trousof
Assistant Examiner—Natalia Harkaway
Attorney, Agent, or Firm—Lawrence S. Levinson; Merle J. Smith; Donald J. Barrack

[57] ABSTRACT

Compounds having the formula

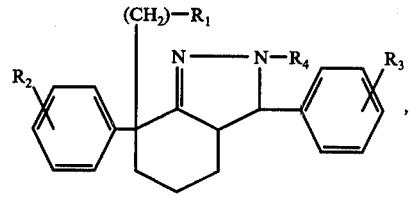

and the pharmaceutically acceptable salts thereof, wherein $R_1$ is alkylamino, dialkylamino or a nitrogen containing heterocyclic group; $R_2$ and $R_3$ are the same or different and are hydrogen, chloro, fluoro, alkyl, alkoxy or trifluoromethyl; $R_4$ is hydrogen, alkyl, 2,2,2-trifluoroethyl, 2-hydroxyethyl, arylalkyl, or alkanoyl; and $n$ is 1, 2 or 3; have useful anti-inflammatory activity.

11 Claims, No Drawings

7-AMINOALKYL-3,7-DIARYL-3,3a,4,5,6,7-HEXAHYDRO-2H-INDAZOLES

SUMMARY OF THE INVENTION

Compounds having the formula

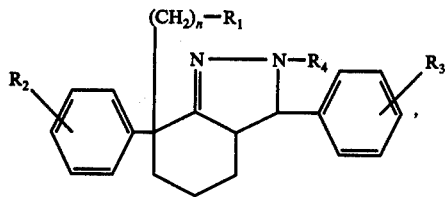

I and the pharmaceutically acceptable salts thereof, possess antiinflammatory activity. In formula I, and throughout the specification, the symbols are as defined below:

$R_1$ is alkylamino, dialkylamino, 1-pyrrolidinyl, 1-piperidinyl, 4-morpholinyl or 4-alkyl-1-piperazinyl;

$R_2$ and $R_3$ are the same or different and are hydrogen, chloro, fluoro, alkyl, alkoxy or trifluoromethyl;

$R_4$ is hydrogen, alkyl, 2,2,2-trifluoroethyl, 2-hydroxyethyl, arylalkyl, or alkanoyl; and $n$ is 1, 2 or 3.

The terms "alkyl" and "alkoxy", as used throughout the specification (whether by themselves or as part of a larger group), refer to groups having 1 to 8 carbon atoms; alkyl and alkoxy groups having 1 to 3 carbon atoms are preferred.

The term "aryl", as used throughout the specification (whether by itself or as part of a larger group), refers to phenyl or phenyl substituted with a chloro, fluoro, alkyl, alkoxy or trifluoromethyl group.

The term "alkanoyl", as used throughout the specification, refers to groups having 2 to 9 carbon atoms.

DETAILED DESCRIPTION OF THE INVENTION

The compounds of this invention wherein $n$ is , 1 are prepared by first reacting a 2-arylcyclohexanone having the formula

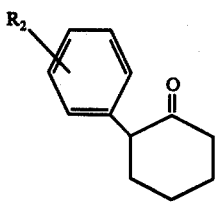

II with a benzaldehyde having the formula

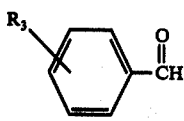

III to yield an intermediate having the formula

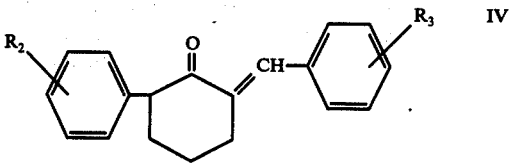

IV

The reaction can be run in an organic solvent; e.g., a lower alkanol such as ethanol, preferably in the presence of alkali. Reaction conditions are not critical and the reaction may conveniently be run at room temperature.

Reaction of a 2-aryl-6-(arylmethylene)cyclohexanone of formula IV with formaldehyde and a compound having the formula $R'_1H$     V using the well-known Mannich reaction, yields an intermediate having the formula

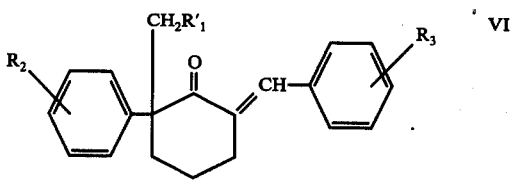

VI

In formulas V and VI, and throughout the specification, the symbol $R'_1$ is alkylbenzylamino, dialkylamino, 1-pyrrolidinyl, 1-piperidinyl, 4-morpholinyl or 4-alkyl-1-piperazinyl.

An intermediate of formula VI can be cyclized by reaction with a hydrazine derivative having the formula $H_2NNHR_4$     VII to yield an indazole derivative having the formula

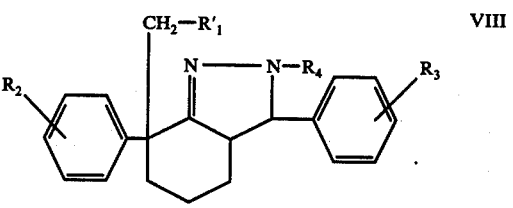

VIII

The reaction can be run in an organic solvent, e.g., a lower alkanol such as methanol. The reaction proceeds most readily when run under reflux conditions.

Those compounds of formula I wherein $R_1$ is alkylamino and $n$ is 1 are prepared by debenzylating a corresponding alkylbenzylamino derivative of formula VIII using the well-known catalytic hydrogenation procedure.

Those compounds of this invention wherein $n$ is 2 or 3 are prepared by first alkylating a 2-arylcyclohexanone of formula II with an aminoalkyl derivative having the formula $R'_1-(CH_2)_{n'}-X$     IX In formula IX, and throughout the specification, the symbol $n'$ is 2 or 3 and the symbol X is chloro or bromo. The alkylation reaction is preferably run at an elevated temperature in an organic solvent, e.g., an aromatic hydrocarbon such as benzene or toluene, in the presence of a cation-forming reagent, e.g., sodium hydride. The alkylated intermediate has the formula

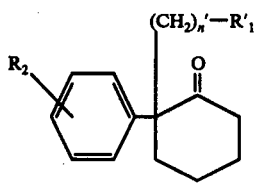
X

An intermediate of formula X can be reacted with a benzaldehyde of formula III to yield an intermediate having the formula

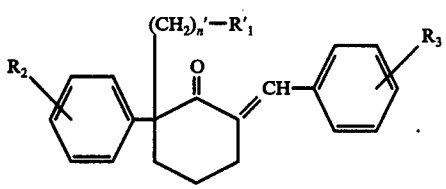
XI

The reaction can be run in the same manner as described above for the reaction of a benzaldehyde of formula III and a 2-arylcyclohexanone of formula II.

An intermediate of formula XI can be cyclized by reaction with a hydrazine of formula VII, using the procedure set forth for the cyclization of a compound of formula VI, to yield an indazole derivative having the formula

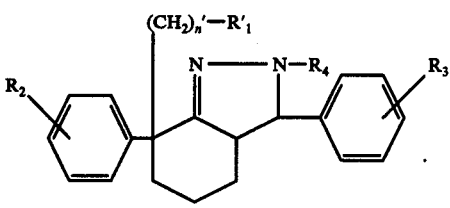
XII

Those compounds of formula I wherein $R_1$ is alkylamino and $n$ is 2 or 3 are prepared by debenzylating a corresponding alkylbenzylamino derivative of formula XII using the well-known catalytic hydrogenation procedure.

Additional processes for preparing the indazole derivatives of this invention will be apparent to a person skilled in the art. For example, those compounds of formula I wherein $R_4$ is alkanoyl are preferably prepared by reacting the corresponding indazole derivative of formula I wherein $R_4$ is hydrogen with the appropriate acid chloride or acid anhydride.

The compounds of formula I may exist as geometric isomers. They can be separated using art-recognized procedures such as crystallization.

The pharmaceutically acceptable salts of the compounds of formula I are readily prepared using procedures well known in the art. Acid addition salts are specifically contemplated. Exemplary salts are the hydrohalides, sulfate, nitrate, phosphate, oxalate, tartrate, maleate, citrate, benzenesulfonate, and others.

The compounds of formula I, and the pharmaceutically acceptable salts thereof, can be used for the treatment of inflammation in mammalian species such as mice, dogs, cats, monkeys, etc. Joint tenderness and stiffness (in conditions such as rheumatoid arthritis) are relieved by the compounds of this invention. Formulation of the compounds can be carried out according to accepted pharmaceutical practice in oral dosage forms such as tablets, capsules, elixirs or powders, or in injectable form in a sterile vehicle. The compounds of this invention can be administered in amounts of about 0.1 to 2.0 grams per 70 kilograms of animal body weight per day, preferably about 0.1 to 1.0 gram per 70 kilograms of animal body weight per day.

Compounds wherein $R_2$ and $R_3$ are hydrogen are specifically contemplated, as are compounds in which $R_4$ is alkyl.

The following examples are specific embodiments of this invention.

EXAMPLE 1

3,3a,4,5,6,7-Hexahydro-N,N,2-trimethyl-3,7-diphenyl-2H-indazole-7-methanamine, monohydrochloride (A) 2-Phenyl-6-(phenylmethylene)cyclohexanone A solution of 60.0 g of 2-phenylcyclohexanone in 400 ml of ethanol is stirred and treated with 160 ml of 15% aqueous sodium hydroxide and 53.0 g of benzaldehyde. The solution is stirred at room temperature and the product begins to separate from the solution as an oil after 30 minutes. The mixture is seeded with crystalline material and allowed to stand for about 16 hours at room temperature. The resulting slurry is poured onto 1.5 l. of ice-water, allowed to stand at room temperature for 2 hours, filtered and washed with cold water to yield 81.2 g of material, melting point 75°-78° C. After crystallization from 200 ml of isopropanol, the product weighs 62.1 g, melting point 85°-87° C. A small sample, recrystallized from ethanol, melts at 86°-88° C.

(B) 2-[(Dimethylamino)methyl]-2-phenyl-6-(phenylmethylene)cyclohexanone, monohydrochloride A mixture of 30.0 g of the above ketone, 18.0 g of dimethylamine, hydrochloride, 15.0 g of paraformaldehyde and 300 ml of ethanol is treated with 5 drops of concentrated hydrochloric acid and then refluxed for 7.5 hours. After standing for about 16 hours, the resulting solution is treated with 10 g of paraformaldehyde and 10 drops of concentrated hydrochloric acid and refluxed for 7.5 hours. The bulk of the solvent is removed on a rotary evaporator and the residue (98 g) is cooled and poured onto 500 ml of cold water. The aqueous phase is cooled and treated portionwise with 35 g of potassium carbonate. The oil which separates is extracted with three 100 ml portions of ether, dried, filtered and evaporated to give 23.8 g of a syrupy residue. The latter is triturated with 50 ml of hexane to give a solid. After cooling overnight, the solid is filtered and dried; weight, 22.0 g, melting point 105°-107° C. Part of the base (17.0 g) is suspended in 100 ml of ethanol (partly soluble), diluted with 100 ml of ether, and the suspension is treated with 8.7 ml of 6.1 N ethanolic hydrogen chloride. The resulting solution is diluted to 600 ml with ether, seeded and cooled to give 15.4 g of solid, melting point 177°-179° C. Partial concentration of the filtrate and dilution with ether gives an additional 1.4 g of material, melting point 177°-179° C.

(C)
3,3a,4,5,6,7-Hexahydro-N,N,2-trimethyl-3,7-diphenyl-2H-indazole-7-methanamine, monohydrochloride A solution of 10.7 g of 2-[(dimethylamino)methyl]-2-phenyl-6-(phenylmethylene)cyclohexanone, monohydrochloride in 70 ml of methanol is treated with 1.5 g of methylhydrazine and the resulting solution is refluxed for 4 hours. The solution is cooled and the solvent is removed on a rotary evaporator to give 13.7 g of a semi-crystalline solid residue, which is crystallized from 30 ml of isopropanol to give 4.2 g of the title compound, melting point 225°–227° C (dec.). An additional 0.77 g of product is recovered from the filtrate giving a total yield of 4.97 g of the title compound, melting point 225°–227° C. Recrystallization of 5.6 g of this material from 100 ml of isopropanol gives 4.8 g of product, melting point 225°–227° C (dec.).

EXAMPLE 2
3,3a,4,5,6,7-Hexahydro-N,N-dimethyl-3,7-diphenyl-2-propyl-2H-indazole-7-methanamine, monohydrochloride 2-[(Dimethylamino)methyl]-2-phenyl-6-(phenylmethylene)cyclohexanone, monohydrochloride (10.7 g, see Example 1B) and 2.5 g of n-propylhydrazine are reacted in 70 ml of methanol at reflux for about 4 hours. The solution is cooled and the solvent is removed on a rotary evaporator to give 13.2 g of partly solid viscous residue. After the residue is dissolved in 60 ml of acetonitrile and diluted with several volumes of ether, a gum precipitates. The liquor is decanted from the gum (1.8 g) and the solvents removed on a rotary evaporator. The residual oil is dissolved in 40 ml of ether; on seeding and rubbing, crystals slowly separate. After cooling for about 16 hours, the feathery material is filtered under nitrogen, washed with ether, and dried to yield 1.0 g of product, melting point 194°–196° C (sintering at 140° C).

The methanol-ether liquor is evaporated and the residue is shaken with 100 ml of water and 200 ml of ether. It appears that a portion of the material is ether soluble. The layers are separated, the aqueous phase extracted with additional ether (200 ml), the combined ether layers dried, and the solvent evaporated to give 6.0 g of a viscous oil.

The above aqueous layer is basified and extracted with potassium carbonate and ether to give 2.0 g of an oil. The oil is dissolved in 10 ml of methanol, treated with 1 ml of 6.1 N alcoholic hydrogen chloride, and diluted to 350 ml with ether. On seeding with the product obtained above, rubbing, and cooling, crystals slowly separate. After cooling for about 16 hours, the product weighs 0.8 g, melting point 190°–193° C (sintering at 135° C). The two solids are combined and crystallized from methanol-ether. The final yield of product is 1.6 g, melting point 194°–196° C (sintering at 140° C).

EXAMPLE 3
3,3a,4,5,6,7-Hexahydro-N,N-dimethyl-3,7-diphenyl-2-propyl-2H-indazole-7-ethanamine, monohydrochloride

(A)
2-[2-(Dimethylamino)ethyl]-2-phenylcyclohexanone, monohydrochloride

A stirred solution of 30 g of 2-phenylcyclohexanone in 450 ml of toluene is treated in 1 portion with 9.0 g of 50% sodium hydride (oil dispersion) and gradually warmed. At about 80°–90° C vigorous foaming occurs. After heating at 105° C for 30 minutes, the solution is allowed to cool to 75° C, treated with 150 ml of 2N 2-dimethylaminoethyl chloride in toluene, and stirred and heated at 100°–105° C for 20 hours; the mixture gradually lightens in color during the heating period.

The cooled mixture is diluted with 450 ml of ether and extracted with a solution of 30 ml of concentrated hydrochloric acid in 300 ml of water, followed by 60 ml of water. In order to hydrolyze the acid-labile basic ether resulting from competing O-alkylation of the enol form of the starting material and thus recover 2-phenylcyclohexanone, the combined aqueous phases are stirred and heated on a steam bath for 7 minutes; an oil separates. After cooling, the partially crystallized oil is extracted with ether twice, and the aqueous phase is basified with 60 g of potassium carbonate and extracted with ether four times to give, following drying and evaporation, 15.1 g of the crude oily product as a base.

The base is dissolved in dichloromethane, treated with 11.4 ml of 5.5 N alcoholic hydrogen chloride, and the solvents removed on a rotary evaporator to give a glass-like residue which is taken up in 75 ml of acetone. On seeding and rubbing, the crystalline hydrochloride salt separates; weight, following 3 days in the cold, 9.7 g, melting point 180°–183° C.

(B)
2-[2-(Dimethylamino)ethyl]-2-phenyl-6-(phenylmethylene)cyclohexanone, monohydrochloride The above intermediate (9.6 g) and 7.4 g of benzaldehyde are reacted in 140 ml of ethanol in the presence of 28 ml of 5 N sodium hydroxide as described in *J. Org. Chem.*, 19, 616 (1954). The mixture is concentrated about ½ way before working up to give 11.3 g of crude product as an oil. The oil is dissolved in dichloromethane, treated with 6.3 ml of 5.5 N alcoholic hydrogen chloride, and the solvents removed on a rotary evaporator. The foamy residue is crystallized from 60 ml of acetone to give 6.1 g of solid; melting point 186°–188° C. A second crop weighing 1.5 g is subsequently obtained; melting point 184°–186° C (sintering at 178° C).

(C)
3,3a,4,5,6,7-Hexahydro-N,N-dimethyl-3,7-diphenyl-2-propyl-2H-indazole-7-ethanamine, monohydrochloride A stirred solution of 6.1 g of the above ketone in 45 ml of methanol is treated with 1.5 g of n-propylhydrazine and refluxed for 4 hours. After standing for about 16 hours, the methanol is removed on a rotary evaporator to give 7.2 g of a foamy residue which is dissolved in 25 ml of acetonitrile and diluted to 300 ml with ether. On seeding and rubbing, the crystalline product gradually separates; yielding, after cooling for about 16 hours, 3.8 g of material, melting point 193°–195° C (sintering at 190° C). Crystallization from 45 ml of acetone gives 2.8 g of material (designated as isomer A) in 2 crops; melting point 198°–200° C. Following recrystallization of the combined crops from 25 ml of acetone, the title compound (isomer A) weighs 2.2 g, melting point 198°–200° C.

The acetonitrile-ether liquor from above is evaporated to give 3.2 g of a glass-like residue which is crystallized from a small volume of acetonitrile and a large volume of ether yielding 2.2 g of material (designated as isomer B) in two crops. Purification of this material by crystallization from 20 ml of acetone gives 1.4 g of the title compound (isomer B) in two crops, melting point 172°–174° C. Recrystallization from 10 ml of acetone gives 0.9 g of the title compound (isomer B), melting point 172°–174° C.

EXAMPLES 4–7

Following the procedure of Example 1, but substituting the hydrochloride salt of the compound listed in column I for dimethylamine hydrochloride and the compound listed in column II for methylhydrazine, yields the hydrochloride salt of the compound listed in column III.

| Column I | Column II | Column III |
|---|---|---|
| pyrrolidine | hydrazine | 3,3a,4,5,6,7-hexahydro-3,7-diphenyl-7-[(1-pyrrolidinyl)methyl]-2H-indazole |
| piperidine | 2,2,2-trifluoroethylhydrazine | 3,3a,4,5,6,7-hexahydro-3,7-diphenyl-7-[(1-piperidinyl)methyl]-2-(2,2,2-trifluoroethyl)-2H-indazole |
| morpholine | 2-hydroxyethylhydrazine | 3,3a,4,5,6,7-hexahydro-2-(2-hydroxyethyl)-7-[(4-morpholinyl)methyl]-3,7-diphenyl-2H-indazole |
| N-methylpiperazine | phenylmethylhydrazine | 3,3a,4,5,6,7-hexahydro-7-[(4-methyl-1-piperazinyl)methyl]-3.7-diphenyl-2-(phenylmethyl)-2H-indazole |

EXAMPLES 8–12

Following the procedure of Example 3, but substituting the compound listed in column I for 2-dimethylaminoethyl chloride and the compound listed in column II for n-propylhydrazine, yields the hydrochloride salt of the compound listed in column III.

| Column I | Column II | Column III |
|---|---|---|
| 3-dimethylaminopropyl chloride | 2,2,2-trifluoroethylhydrazine | 3,3a,4,5,6,7-hexahydro-7-[3-(dimethylamino)propyl]-3,7-diphenyl-2-(2,2,2-trifluoroethyl)-2H-indazole |
| 2-(1-pyrrolidinyl)ethyl chloride | 2-hydroxyethylhydrazine | 3,3a,4,5,6,7-hexahydro-2-(2-hydroxyethyl)-3,7-diphenyl-7-[2-(1-pyrrolidinyl)ethyl]-2H-indazole |
| 3-(1-piperidinyl)propyl chloride | 2-phenylethylhydrazine | 3,3a,4,5,6,7-hexahydro-3,7-diphenyl-2-(2-phenylethyl)-7-[3-(1-piperidinyl)propyl]-2H-indazole |
| 2-(4-morpholinyl)ethyl chloride | hydrazine | 3,3a,4,5,6,7-hexahydro-7-[2-(4-morpholinyl)ethyl]3,7-diphenyl-2H-indazole |
| 3-(4-ethyl-1-piperazinyl)propyl chloride | methylhydrazine | 3,3a,4,5,6,7-hexahydro-7-[3-(4-ethyl-1-piperazinyl)propyl]-2-methyl-3,7-diphenyl-2H-indazole |

EXAMPLES 13–17

Following the procedure of Example 1, but substituting the compound listed in column I for 2-phenylcyclohexanone and the compound listed in column II for benzaldehyde, yields the hydrochloride salt of the compound listed in column III.

| Column I | Column II | Column III |
|---|---|---|
| 2-(p-chlorophenyl)cyclohexanone | p-chlorobenzaldehyde | 3,3a,4,5,6,7-hexahydro-3,7-bis-(p-chlorophenyl)-N,N,2-trimethyl-2H-indazole-7-methanamine |
| 2-(m-trifluoromethylphenyl)cyclohexanone | m-trifluoromethylbenzaldehyde | 3,3a,4,5,6,7-hexahydro-3,7-bis-(m-trifluoromethylphenyl)-N,N,2-trimethyl-2H-indazole-7-methanamine |
| 2-(o-methylphenyl)cyclohexanone | o-methylbenzaldehyde | 3,3a,4,5,6,7-hexahydro-3,7-bis-(o-methylphenyl)-N,N,2-trimethyl-2H-indazole-7-methanamine |
| 2-(o-ethoxyphenyl)cyclohexanone | benzaldehyde | 3,3a,4,5,6,7-hexahydro-7-(o-ethoxyphenyl)-N,N,2-trimethyl-3-phenyl-2H-indazole-7-methanamine |
| 2-phenylcyclohexanone | p-fluorobenzaldehyde | 3,3a,4,5,6,7-hexahydro-3-(p-fluorophenyl)-N,N,2-trimethyl-7-phenyl-2H-indazole-7-methanamine |

EXAMPLE 18

3,3a,4,5,6,7-Hexahydro-N,2-dimethyl-3,7-diphenyl-2H-indazole-7-methanamine, monohydrochloride (A)

N-Benzyl-3,3a,4,5,6,7-hexahydro-N,2-dimethyl-3,7-diphenyl-2H-indazole-7-methanamine, monohydrochloride Following the procedure of Examples 1B and 1C, but substituting N-benzyl-N-methylamine, hydrochloride for dimethylamine, hydrochloride, yields the title compound.

(B)

3,3a,4,5,6,7-Hexahydro-N,2-dimethyl-3,7-diphenyl-2H-indazole-7-methanamine, monohydrochloride A suspension of 10 parts of material from part A in 100 ml of ethanol is treated with 1 part of 5% palladium on carbon, placed under 3 atmospheres of gaseous hydrogen and shaken until 1 equivalent of hydrogen is consumed. The mixture is filtered to remove the catalyst and the solvent is evaporated under reduced pressure to yield the title compound.

EXAMPLE 19

3,3a,4,5,6,7-Hexahydro-2-acetyl-3,7-diphenyl-7-[(1-pyrrolidinyl)methyl]-2H-indazole, monohydrochloride A stirred suspension of 7.5 g of 3,3a,4,5,6,7-hexahydro-3,7-diphenyl-7-[(1-pyrrolidinyl)methyl]-2H-indazole, monohydrochloride (see Example 4) in 75 ml of acetic anhydride is heated at reflux for about 4 hours. The solvent is evaporated to give the product.

What is claimed is:

1. A compound having the formula

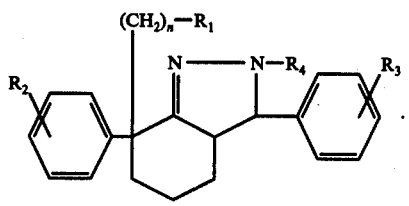

or a pharmaceutically acceptable salt thereof, wherein
$R_1$ is alkylamino, dialkylamino, 1-pyrrolidinyl, 1-piperidinyl, 4-morpholinyl or 4-alkyl-1-piperazinyl;
$R_2$ and $R_3$ are the same or different and are hydrogen, chloro, fluoro, alkyl, alkoxy or trifluoromethyl;
$R_4$ is hydrogen, alkyl, 2,2,2-trifluoroethyl, 2-hydroxyethyl, arylalkyl, or alkanoyl;
$n$ is 1, 2 or 3; and
wherein the terms "alkyl" and "alkoxy" refer to groups having 1 to 8 carbon atoms, the term "aryl" refers to phenyl or phenyl substituted with a chloro, fluoro, alkyl, alkoxy or trifluoromethyl group, and the term "alkanoyl" refers to groups having 2 to 9 carbon atoms.

2. A compound in accordance with claim 1 wherein $n$ is 1.

3. A compound in accordance with claim 1 wherein $n$ is 2 or 3.

4. A compound in accordance with claim 1 wherein $R_1$ is alkylamino or dialkylamino.

5. A compound in accordance with claim 4 wherein $R_1$ is dialkylamino.

6. A compound in accordance with claim 1 wherein $R_1$ is 1-pyrrolidinyl, 1-piperidinyl, 4-morpholinyl or 4-alkyl-1-piperazinyl.

7. A compound in accordance with claim 1 wherein $R_2$ and $R_3$ are hydrogen.

8. A compound in accordance with claim 1 wherein $R_4$ is alkyl.

9. The compound in accordance with claim 1, 3,3a,4,5,6,7-hexahydro-N,N,2-trimethyl-3,7-diphenyl-2H-indazole-7-methanamine, monohydrochloride.

10. The compound in accordance with claim 1, 3,3a,4,5,6,7-hexahydro-N,N-dimethyl-3,7-diphenyl-2-propyl-2H-indazole-7-methanamine, monohydrochloride.

11. The compound in accordance with claim 1, 3,3a,4,5,6,7-hexahydro-N,N-dimethyl-3,7-diphenyl-2-propyl-2H-indazole-7-ethanamine, monohydrochloride.

* * * * *